United States Patent [19]

Moretti

[11] Patent Number: 6,040,346
[45] Date of Patent: Mar. 21, 2000

[54] USE OF L-CARNITINE AND DERIVATIVES FOR REDUCING CERAMIDE LEVELS AND POTENTIATING ANTIRETROVIRAL DRUGS

[75] Inventor: Sonia Moretti, Rome, Italy

[73] Assignees: Sigma-Tau Industrie Farmaceutiche Riunite S.p.A.; Mendes s.r.l., both of Rome, Italy

[21] Appl. No.: 09/000,202

[22] PCT Filed: Jul. 19, 1996

[86] PCT No.: PCT/IT96/00146

§ 371 Date: Feb. 3, 1998

§ 102(e) Date: Feb. 3, 1998

[87] PCT Pub. No.: WO97/05864

PCT Pub. Date: Feb. 20, 1997

[30] Foreign Application Priority Data

Aug. 3, 1995 [IT] Italy ................................. RM95A0544

[51] Int. Cl.$^7$ ............................ A01N 33/12; A01N 43/04
[52] U.S. Cl. .............................................. 514/642; 514/50

[58] Field of Search ........................................ 514/642, 50

[56] References Cited

U.S. PATENT DOCUMENTS 4,194,006  3/1980  Cavazza .................................. 424/311

OTHER PUBLICATIONS

DeSimone et al, "High Dose L–Caritine Improves Immunologic and Metabolic Parameters in AIDS Patients", Immunopharmacology and Immunotixicology, 15(1), pp. 1–12, 1993.

*Primary Examiner*—Russell Travers
*Attorney, Agent, or Firm*—Oblon, Spivak, McClelland, Maier & Neustadt, P.C.

[57] ABSTRACT

The present invention provides a novel use of L-carnitine, the derivatives thereof and their pharmacologically acceptable salts in combination with antiretroviral drugs for reducing ceramide levels and enhance the activity of the aforesaid antiretroviral drugs for the therapeutic treatment of HIV-infection and AIDS.

6 Claims, No Drawings

USE OF L-CARNITINE AND DERIVATIVES FOR REDUCING CERAMIDE LEVELS AND POTENTIATING ANTIRETROVIRAL DRUGS

The present invention relates to a novel therapeutic use of L-carnitine, the derivatives thereof and their pharmacologically acceptable salts in combination with antiretroviral drugs for the therapeutic treatment of HIV-infection and AIDS. More particularly, the present invention relates to the use of L-carnitine, acyl L-carnitines wherein the acyl group, straight or branched, has 2–6 carbon atoms, and the pharmacologically acceptable salts thereof in combination with nucleoside-like inhibitors of reverse transcriptase, non-nucleoside inhibitors of reverse transcriptase and inhibitors of HIV protease, for reducing ceramide levels and enhance the activity of the aforesaid antiretroviral drugs in HIV-infected patients.

Most of the pathogenetic mechanisms that contribute to the progression of infection due to human immunodeficiency virus 1 or 2 (HIV-1, HIV-2) are directly or indirectly related to the state of general activation of the immune system.

Chronic activation of the immune system potentiates viral replication both via secretion of a number of cytokines favouring HIV expression and by maintaining a reserve of activated immune cells which act as targets for the HIV and facilitate its replication.

Moreover, the state of persistent activation of the immune system induces abnormalities of such a nature (e.g. an increased apoptosis) as to lead to a progressive weakening of the immune responses.

A vicious circle is thus set up: progressive loss of competence of the immune system→viral dissemination→reduced elimination of the virus→chronic activation of the immune system. The above process may last for years until such a marked deterioration of the immune system occurs as to lead to an uncontrolled viral replication and to the onset of opportunist infections, or to the development of acquired immuno-deficiency syndrome (AIDS).

On the basis of the pathogenetic mechanisms outlined above, it appears dear that any anti-HIV treatment must be aimed at reducing viral replication and at blocking the deterioration of the immune system.

As regards antiretroviral therapy, unfortunately HIV is characterized by a high degree of genetic variability originating above all in the very substantial lack of precision of reverse transcriptase. The retroviral enzyme lacks enzymatic systems for the control of possible transcription errors. The result is the emergence of variants of the virus—over a range which is a function of viral replication—which are responsible for the progressive eluding of the immune system and of resistance to antiretroviral drugs. In the case of zidovudine (AZT, ZDV) the loss of clinical efficacy in situations of monotherapy is an extensively acknowledged fact. Even the anti-retroviral agents discovered more recently, e.g. zalcitabine [ddc], didanosine [ddI] and lamivudine [3TC] suffer from the same drawback.

It has recently been demonstrated that ceramide stimulates HIV expression. What is more, ceramide is one of the factors capable of inducing cellular apoptosis, a phenomenon which is increased in subjects with HIV infection and which contributes to the depletion of TCD4 and TCD8 lymphocytes. It thus appears evident that changes in the concentration or metabolism of ceramide may affect the viral load and cellular apoptosis in HIV-infected subjects (Papp B. et al., AIDS, Res. Hum. Retrovirus, 10(7), 775–80).

Surprisingly, it has now been found that L-carnitine and derivatives thereof, i.e. the acyl L-carnitines wherein the acyl group, straight or branched has 2–6 carbon atoms and the pharmacologically acceptable salts thereof inhibit ceramide synthesis by at least 25% and when they are used in combination with antiretroviral drugs such as e.g. AZT, stavudine [d4T], fluorothymidine [FLT], azidouridine [Azdu], phosphonated acyclic nucleosides [PMEA], HIV-1 specific nucleosides ([TSAO], zalcitabine [ddC], didanosine [ddI] and lamivudine [3TC], dipyridodiazepinones, tetrahydroimidazobenzodiazepinones, pyridones or L drugs, bis-heteroarylpiperazines, derivatives of alpha-anilinophenylacetamide, derivatives of quinaxoline, Ro-31-8959, U-81749, KNI-227, SC-52151, HOE/BAY 793 and the like, enhance the antiretroviral activity and defense of the immune system exerted by these drugs.

Pharmaceutically acceptable salts of L-carnitine or acyl L-carnitine include, in addition to the inner salts, any salt of these with acids which do not give rise to undesirable toxic or collateral effects. These acids are well known to the average skilled pharmacologists and experts in pharmaceutical technology.

Non-limiting examples of suitable salts include the chloride; bromide; iodide; aspartate, particularly acid aspartate; citrate, particularly acid citrate; tartrate; phosphate, particularly acid phosphate; fumarate, particularly acid fumarate; glycerophosphate; glucose phosphate; lactate; maleate, particularly acid maleate; orotate; oxalate, particularly acid oxalate; sulphate, particularly acid sulphate; tricholoroacetate; trifluoroacetate and methanesulphonate.

Particularly preferred are L-carnitine, acetyl, propionyl, butyryl, valeryl and isovaleryl L-carnitine.

The combined administration of L-carnitine and its derivatives as defined above plus an antiretroviral agent is generally conducted via the oral or parenteral routes at daily doses ranging from 1 to 500 mg/kg, with a particular preference for doses from 20 to 100 mg/kg, in a ratio of L-carnitine and its derivatives as defined above to the antiretroviral agent ranging from 1:40 to 40:1, with a particular preference for ratios from 1:10 to 10:1.

Conveniently, the administration will take the form of a unit dose including both active ingredients and this may also include excipients and additional active ingredients well-known to those skilled in this art, such as, for instance, dextran, TNF-alpha inhibitors (e.g. pentoxyphylline), glutathione and other antioxidant drugs (e.g. acetylcysteine), immuno-modulatory drugs, immunosuppressive or chemotherapeutic agents, vitamins and oligoelements.

Lastly, it should be noted that everything suggests that other basic amino acids, particularly lysine, basic amino acid acyl derivatives and their pharmaceutically acceptable salts are capable of reducing the levels of ceramide and of potentiating the activity of antiretroviral drugs for the therapeutic management of HIV infection and AIDS.

The purpose of the examples that follow here below is to illustrate the invention and they should not be construed as in any way limiting the range of possibilities.

EXAMPLE 1

The effect of administration of a combination of L-carnitine (8 g daily by mouth for 4 weeks) plus AZT (600 mg daily by mouth) on 13 patients suffering from AIDS with normal serum and intracellular levels of carnitine and acetylcarnitine, who had previously been submitted to treatment with AZT (600 mg daily by mouth) for at least 6 months, was evaluated.

The determinations were carried out prior to the combined treatment, while patients were taking only AZT (T0), after 4 weeks of therapy with the L-carnitine-AZT combination (T1) and one month after discontinuation of treatment with L-carnitine (T2), leaving the patients on AZT alone. TCD4 lymphocytes were measured by flow cytometry by means of a specific monoclonal antibody (number of lymphocytes per $mm^3$) and the apoptotic lymphocytes by flow cytometry after staining with propydium iodide, quantifying the cells with hypodiploid nuclei (number of lymphocytes per 50,000 cells). The viral load (number of viral particles per ml of serum) was determined by quantifying HVI-1 RNA by means of a polymerase chain reaction (Amplicor HIV detection system by Roche). The Wilcoxon test was used for the statistical processing.

The results are shown in Table 1 here below.

TABLE 1

| Patient | TCD4 lymphoycytes/$mm^3$ | | | Apoptotic lymphocytes/ 50,000 cells | | | HIV (viral particles per ml) | |
|---|---|---|---|---|---|---|---|---|
| | T0 | T1 | T2 | T0 | T1 | T2 | T0 | T1 |
| 1 | 195 | 211 | 172 | 85 | 59 | 130 | 3,500 | 900 |
| 2 | 239 | 254 | 264 | 112 | 37 | 84 | 2,400 | 1,600 |
| 3 | 172 | 176 | 176 | 90 | 29 | 35 | 2,800 | 1,600 |
| 4 | 254 | 287 | 279 | 91 | 40 | 39 | 1,700 | 1,500 |
| 5 | 141 | 165 | 165 | 59 | 47 | 66 | 62,000 | 1,100 |
| 6 | 125 | 205 | 146 | 280 | 81 | 36 | 2,200 | 2,000 |
| 7 | 40 | 51 | 47 | 41 | 26 | 88 | 3,800 | 3,100 |
| 8 | 309 | 423 | 411 | 82 | 67 | 41 | 5,900 | 3,900 |
| 9 | 303 | 502 | 402 | 102 | 20 | 41 | 5,300 | 3,300 |
| 10 | 47 | 46 | 43 | 65 | 42 | 64 | 2,300 | 2,300 |
| 11 | 120 | 120 | 116 | 52 | 52 | 55 | 1,400 | 1.400 |
| 12 | 52 | 60 | 41 | 148 | 111 | 104 | 900 | 1,300 |
| 13 | 26 | 378 | 378 | 113 | 38 | 54 | 43,000 | 7,000 |
| Mean | 178 | 221 | 203 | 101 | 50 | 64 | 10,553 | 2,384 |
| S.D. | 101 | 144 | 133 | 61 | 25 | 64 | 19,070 | 1,661 |
| Statistical significance | | 0.001 | 0.02 | | 0.001 | 0.04 | | 0.004 |

In the same subjects the levels of lymphocyte ceramide, measured by means of DAG (diacylglycerol) kinase assay (Cifone M. G. et al., J. Exp. Med., 180(4), 1547–52) dropped from $48\pm8$ pmol/$10^6$ lymphocytes measured prior to combination treatment (T0) to $27\pm5$ pmol/$10^6$ lymphocytes (T1) (P<0.01), rising again to $38\pm9$ pmol/$10^6$ lymphocytes one month after discontinuation of L-carnitine (T2).

These results clearly show that treatment with AZT alone, even when prolonged previously for more than 6 months (T0), does not afford those immunological and virological improvements that are achievable with the L-carnitine-AZT combination in only 4 weeks (T1). These improvements tend to decline on discontinuing treatment (T2).

EXAMPLE 2

Four subjects with AIDS were treated with 600 mg of AZT daily by mouth. Of these, two were also treated with L-carnitine 3 g daily. The total duration of the treatment was 6 months. Muscle biopsies were performed before and after treatment. The ceramide present at muscle cell level was determined before and after treatment, after sonicating and homogenizing the biopsy material. The viral load was determined in the same muscle homogenates, as described in Example 1.

The results are shown in Table 2 here below.

TABLE 2

| | Pre-treatment ceramide (pmol/mg protein) | Post-treatment ceramide (pmol/mg protein) | Pre-treatment HIV (viral particles/mg protein) | Post-treatment HIV (viral particles/mg protein) |
|---|---|---|---|---|
| Patient 1 (AZT) | 89 | 95 | 3,800 | 4,100 |
| Patient 2 (AZT) | 95 | 103 | 5,900 | 5,800 |
| Mean | 92 | 99 | 4,850 | 4,950 |

TABLE 2-continued

| | Pre-treatment ceramide (pmol/mg protein) | Post-treatment ceramide (pmol/mg protein) | Pre-treatment HIV (viral particles/mg protein) | Post-treatment HIV (viral particles/mg protein) |
|---|---|---|---|---|
| S.D. | 4 | 6 | 1,485 | 1,202 |
| Statistical significance | | n.s. | | n.s. |
| Patient 3 (AZT + L-carnitine) | 129 | 39 | 10,200 | 3,200 |
| Patient 4 (AZT + L-carnitine) | 79 | 27 | 5,100 | 1,300 |
| Mean | 104 | 33 | 7,650 | 4,950 |
| S.D. | 35 | 8 | 3,606 | 1,344 |
| Statistical significance | | 0.01 | | 0.05 |

It is apparent that treatment with the L-carnitine-AZT combination is distinctly more effective in reducing the viral load and levels of ceramide, also at muscle level, compared to treatment with AZT alone.

What is claimed is:

1. A method of potentiating the anti-retroviral activity of AZT effective in the treatment of a patient with normal serum and intracellular levels of carnitine and acetylcarnitine and suffering from AIDS, comprising administering to a patient in need thereof:

a) AZT; and b) an enhancement agent selected from the group consisting of L-carnitine, an alkanoyl L-carnitine wherein the alkanoyl group has 2–6 carbon atoms, and pharmacologically acceptable salts, or mixtures thereof, wherein the enhancement agent and the AZT are administered for at least 4 weeks in amounts effective to increase TCD4 lymphocyte levels.

2. The method of claim 1, wherein the patient had previously been treated with AZT for at least 6 months.

3. A method for reducing ceramide levels in the muscles of a patient suffering from AIDS, comprising:

administering to said patient AZT and L-carnitine for at least 4 weeks in amounts effective to increase TCD4 lymphocyte levels.

4. The method of claim 1, wherein said patient is treated with 8 g daily of L-carnitine or an alkanoyl L-carnitine, for at least four weeks.

5. The method of claim 1, wherein said patient is treated with 3 g daily of L-carnitine or an alkanoyl L-carnitine for at least six months.

6. The method of claim 1, wherein 600 mg daily of AZT is administered orally.

* * * * *